United States Patent [19]

Danby

[11] 4,380,235
[45] Apr. 19, 1983

[54] METERED DROP DISPENSERS
[75] Inventor: Hal C. Danby, Palo Alto, Calif.
[73] Assignee: Anatros Corporation, Palo Alto, Calif.
[21] Appl. No.: 259,436
[22] Filed: May 1, 1981
[51] Int. Cl.³ .................. A61M 5/00; B65D 47/18
[52] U.S. Cl. .................................. 604/251; 222/420
[58] Field of Search ............... 128/214, 214 C; 222/420, 421; 30/332

[56] References Cited

U.S. PATENT DOCUMENTS

| | | | |
|---|---|---|---|
| 1,824,394 | 9/1931 | Crane | 222/420 X |
| 2,877,547 | 3/1959 | Feaster | 30/322 |
| 3,276,639 | 10/1966 | Lancaster | 222/421 |
| 3,311,628 | 3/1967 | Fields | 128/214 C |
| 3,323,691 | 6/1967 | Ruetz | 222/421 X |

FOREIGN PATENT DOCUMENTS

| | | | |
|---|---|---|---|
| 1164 | of 1883 | United Kingdom | 30/322 |
| 297017 | 7/1927 | United Kingdom | 30/322 |
| 931327 | 6/1963 | United Kingdom | 30/322 |

*Primary Examiner*—Stephen C. Pellegrino
*Attorney, Agent, or Firm*—Harvey G. Lowhurst

[57] ABSTRACT

A metered drop dispenser utilizing a drop former in which the facing end walls of a pair of coplanar, spaced apart plate members form a channel which is open on two sides and which has outwardly flared end portions at the channel exit.

7 Claims, 6 Drawing Figures

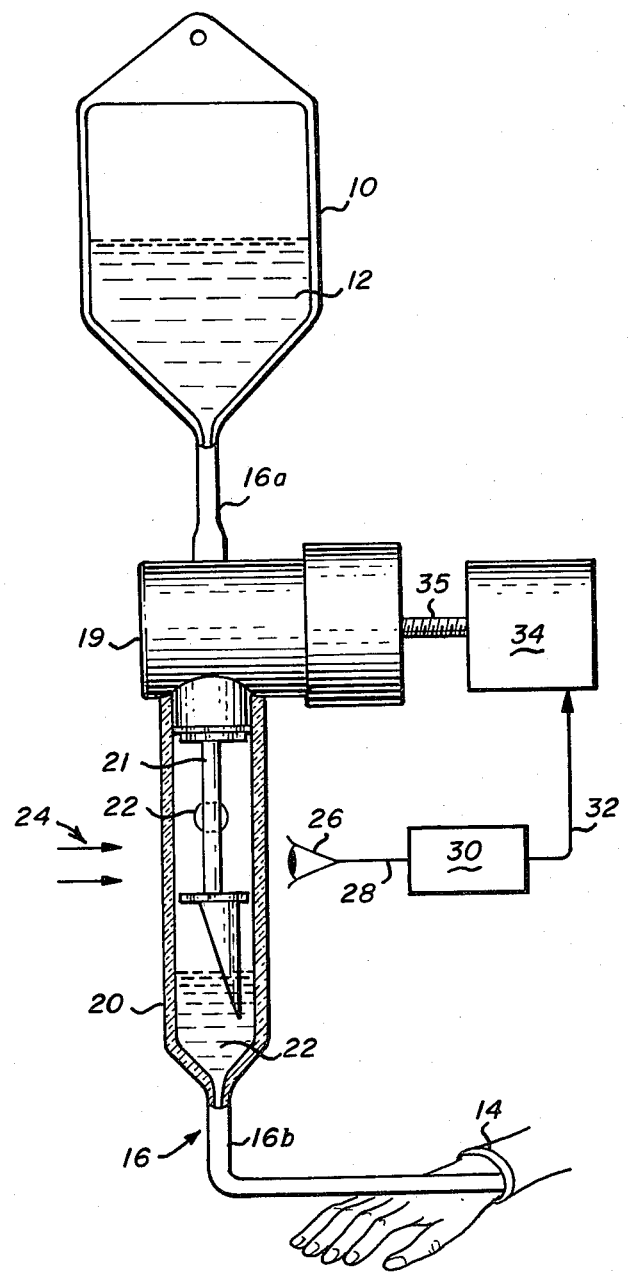
Fig_1

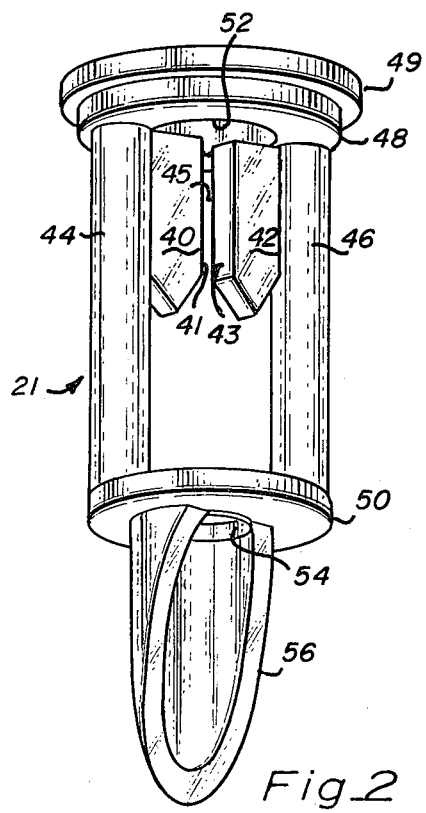
Fig_2
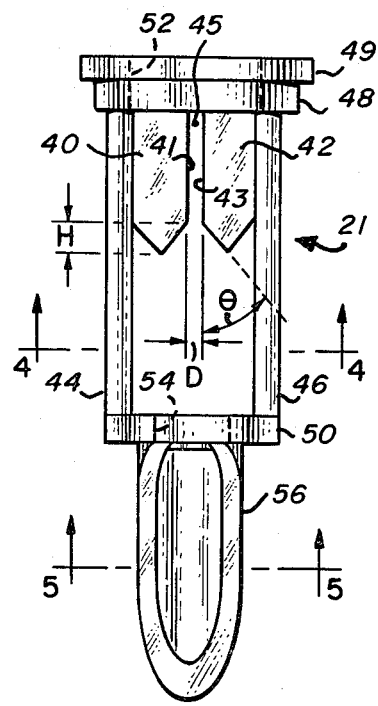
Fig_3
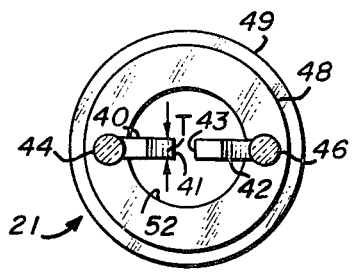
Fig_4
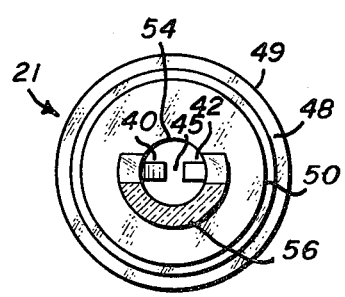
Fig_5
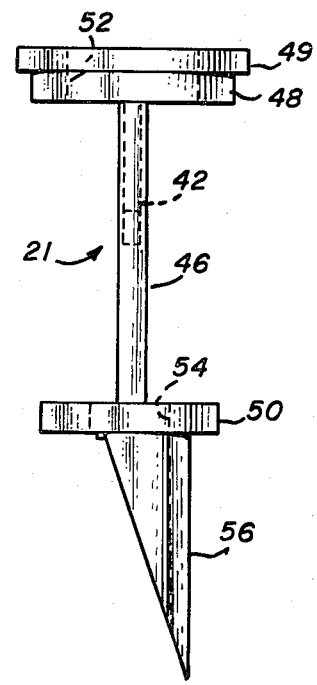
Fig_6

METERED DROP DISPENSERS

BACKGROUND OF THE INVENTION

This invention relates to an improvement in disposable liquid dispensing apparatus, and more particularly to such an apparatus for the intravenous or enteric infusion of accurately measured amounts of liquid, such as medicaments or nutrients, to a patient.

When intravenously or enterically infusing liquids into a patient, it is often desirable and sometimes absolutely necessary to control the specific amount of fluid which is to be administered, as well as the rate of administration, so that the accurate control of dosage is possible. It is conventional in such dispensing apparatus to provide a separate drip or drop counting chamber in the liquid conveying conduit between a liquid supply reservoir and the patient to provide a visual flow indication of the liquid being administered. The determination of the dose is usually made by providing some drop forming means at the upper end of the drop count chamber, and counting the drops falling to the bottom of the drip chamber from which the liquid is conveyed to the patient.

Conventionally, the dosage is determined by calibration of the drop count per unit time multiplied by the volume of liquid contained in each drop. The drop size is determined by the physical configuration of the drop forming means and is usually fixed for each drop forming means, and the drop rate is conventionally controlled by a pinch type device which clamps or restricts the flow through the liquid conveying conduit.

Since the entire liquid dispensing apparatus, also referred to as a fluid administration set or an IV (intravenous) set, has to retain sterile integrity, they are generally of the disposable or throw away after use type. This requires it to be inexpensive to manufacture, and since accurate control of the dosage requires drops of the same volume from IV set to IV set, the drop forming means must be the same for each IV set.

The conventional drop forming means for a disposable IV set is a molded plastic part, such as the stopper illustrated in U.S. Pat. No. 3,311,268, which closes the upper end of the drop counting chamber and which has a passage therethrough whose diameter is preselected to dispense drops of a certain size. It is well known to those skilled in the art that the size of the drops released from such a passage is usually a function of the diameter of the passage. Such drop forming means-stoppers are generally formed by a female injection molding die utilizing a slightly tapered male injection molding die to form the drop forming liquid passage. One of the problems encountered in the mass production of such drop forming means is that dies wear out because of sliding friction between the male part of the die and the molded piece, and after the molding of several hundred thousands of prior art drop formers, the constant wear on the tapered male injection molding die makes the same smaller with use and thereby reduces the diameter of the drop forming passage, and thereby the volume of the drops it forms.

Since the disposable drop chamber is generally inserted into a permanent metering means which determines the drop rate and actuates a drop rate control means to adjust the drop rate for the desired dosage, it becomes of utmost importance that the volume of the drops formed remains constant from drop former to drop former, else it becomes necessary to calibrate each disposable liquid administration set prior to utilization.

U.S. Pat. No. 3,276,639 discloses one form of a drop former for dispensing drops of liquid of uniform and accurately predetermined volume. That patent proposes to provide a special drop forming element at the end of a drop forming passage in the form of a tube which has a flared discharge opening. While this extension may accomplish the stated objects and provide drops of a desired volume, if it is also an injection molded part, the dies producing this part will wear after many uses causing a slight and continuous change in the dimension of the parts whereby this particular drop former suffers from the same deficiency, namely the inability of each manufactured drop former to deliver drops of the same precise and uniform volume as the manufacturing dies for producing these extensions start to wear.

OBJECTS OF THE PRESENT INVENTION

It is therefore an object of the present invention to provide a drop forming means which has a configuration to produce drops of the same, uniform, accurately predetermined volume.

It is a further object of the present invention to provide a drop forming means which is inexpensive to manufacture, and which can be mass-produced without wear of the tools and therefor without a change in the critical dimensions which determine drop volume.

It is another object of the present invention to provide a drop forming means which produces drops of uniform predetermined volume from drop former to drop former, and in which the exact geometry of the parts of the drop forming means which are determinative of drop volume are easily maintained during the manufacture of the drop forming means.

SUMMARY OF THE INVENTION

In accordance with the present invention, there is provided a metered drop dispenser for inserting in the liquid conveying means in which the drop forming means includes a pair of coplanar and spaced apart plate members of uniform thickness which have parallel, planar, facing end walls separated a predetermined distance, with a flare or taper forming the exit portion.

BRIEF DESCRIPTION OF THE DRAWINGS

FIG. 1 is a schematic elevational view of an embodiment of the invention in operative association with the fluid administration set;

FIG. 2 is a perspective, enlarged view of the drop former disposed at the upper end of the drop counting chamber of FIG. 1;

FIG. 3 is a reduced elevational view of the drop former of FIG. 2;

FIG. 4 is a cross sectional view taken along lines 4—4 of FIG. 3;

FIG. 5 is a cross sectional view taken along lines 5—5 of FIG. 3; and

FIG. 6 is a side elevational view taken along lines 6—6 of FIG. 3.

DETAILED DESCRIPTION OF THE DRAWINGS

Referring now to FIG. 1 of the drawings, there is shown a schematic plan view of an IV set having a fluid container 10 housing a liquid 12 which is to be administered to a patient, such as is illustrated by the artist's rendition of a hand-arm portion 14. Container 10 is connected to patient 14 through a liquid conveying means 16 which is divided into an upstream or upper portion 16a and a downstream or lower portion 16b, a control valve 19 connected to upper portion 16a, and a drip or drop counting chamber 20 connecting valve 19 to lower portion 16b. Chamber 20 supports a drop forming means 21 in its interior which will be explained hereinafter, and has transparent side walls so that drops, such as 22, can be counted when they interrupt the beam of light, from a light source diagrammatically illustrated at 24, which passes through chamber 20 to a photodiode 26. The output lead 28 from photodiode 26 is connected to a comparator 30 which provides an electrical control signal on output lead 32 for activating a stepping motor 34 whose lead screw 35 performs a control function in manifold valve 19 as is explained in detail in copending patent application Ser. No. 229,350, filed on Jan. 29, 1981, and assigned to the same assignee as the present invention. At the lower end of drop chamber 20, the drops collect into a pool as shown at 23 from which the liquid flows into lower conveying means 16b.

The means for and the method of counting drops, developing a signal commensurate with the actual drop count, comparing this signal with another signal commensurate with a desired drop count within comparator 30, and developing a control signal on lead 32 which is commensurate with the difference between the desired and the actual count, forms no part of this invention since there are numerous prior art devices which will provide a suitable control signal.

The present invention can be used with any of the prior art counting devices which provide an actual count, compare the actual count with a desired count, and develop a control signal in case that the actual count does not accurately agree with the desired count. Further, even though the invention is explained with reference to an IV set, as illustrated in FIG. 1, it is also to be understood that drop forming means 21 of the present invention is applicable in exactly the same manner to an enteric feeding set in which a container, such as 10, is filled with an enteric fluid rather than an intravenous fluid 12, and fluid passage 16b is placed into the gastrointestinal tract rather than a vein. Further, drop forming means 21 is useful in any application requiring the forming of drops of a predetermined precise volume from a mass-produced drop former.

Referring now to FIGS. 2-6, there is shown drop forming means 21 of the present invention which is easily mass-produced, with negligible wear and tear on the mold tools, and which provide drops of the exact same volume from drop former to drop former. Drop former 21 is a molded part and comprises a pair of coplanar, spaced apart plate members 40 and 42, a pair of vertical circular columns 44 and 46 and an upper annulus 48 and lower annulus 50. Plate members 40 and 42 define a pair of spaced apart, opposite end walls 41 and 43 forming a flow channel 45 which has two closed sides, namely end walls 41 and 43 and two open sides.

Even though the plate members, vertical columns and annuli are a one part mold, it is to be understood that those parts may be stamped or otherwise manufactured separately and thereafter assembled by gluing or otherwise affixing these six parts to one another.

Upper annulus 48 has a peripheral surface to fit snugly into drip chamber 20 and an upper, outwardly extending shoulder 49 which rests on the upper edge of drip chamber 20 to support drop former 21. Upper annulus 48 also has a central opening 52 which is generally coextensive with the opening in valve 19, and if no valve is placed directly above drip chamber 20, then it is coextensive with portion 16a. In the preferred embodiment of the present invention, annulus 48 is coupled directly to control valve 19 with liquid passing through opening 52 to the space between plate members 40 and 42. Attached to lower annulus 50, which likewise has a central opening 54 which is generally of the same size as opening 52, is a splash preventer which may be molded or formed of a piece of tubing sliced diagonally to form a taper to provide an elongated opening. The splash preventer in combination with lower annulus 50 prevents liquid from being splashed into the portion of chamber 20 through which the light beam passes and thereby guards against an erroneous count.

The volume of the drop provided by drop former 21 is, generally speaking, a function of four physical dimensions, namely the average distance of separation between facing end walls 41 and 43 of plate members 40 and 42 which is designated as "D", the average thickness of plate members 40 and 42 which is designated as "T", the slant angle at the exit portion of channel 45 formed between plate members 40 and 42 which is designated as "$\theta$", and the vertically projected length of the tapered exit portion of channel 45 which is designated as "H". Careful experiments have resulted in the following values of drop volume in milliliters for a drop former 21 having a plate member 40 and 42 thickness "T" equal to 0.030 inches and an exit angle "$\theta$" equal to 40 degrees:

| H in inches | D in inches | Volume in ml |
|---|---|---|
| 0.095 | 0.046 | 0.059 |
| 0.095 | 0.044 | 0.057 |
| 0.065 | 0.046 | 0.050 |

It has further been found that, even though the drop volume is a function of the thickness of the plate members, the separation of the plate members, as well as of the degree and length of the taper, it is substantially independent of the length of the plate member faces 41 and 43. In other words, as long as the length of channel 45 is at least twice the plate member separation, the drop size does not materially vary with channel length.

In the manufacture of drop former 21, it should be understood that the dies suffer much less frictional wear due to sliding friction between the die and the molded part when compared to the prior art male die with the long taper to form the liquid passage. Accordingly, the thickness of the plate members as well as the separation of faces 41 and 43 is not subjected to much wear and tear of the dies. The same is true of the angle and of the length of the tapered portion of the channel exit. Since none of the other dimensions is critical, the drop former of this invention can be mass produced with adequate assurances that the first drop former as well as the millionth drop former will have the identical same dimension, and therefor provide the identical drop volume. Further, to facilitate molding the drop former, and particularly the ejection from the mold, it has been found desirable to slightly taper end walls 41 and 43 and the faces of plate members 40 and 42. This slight taper of the channel and the plate members has been found not to materially affect the action of the drop former, and the distance "D" is the average channel width and the thickness "T" is the average plate thickness.

Even though it is believed that the uniformity of drop volume from drop former to drop former is due to the ability of the die to maintain a more constant dimensional integrity—due to negligible wear with use—it is to be understood that there may also be other explanations for the drop volume uniformity. One theory advanced is that the open channel allows the drop to be formed with reliance on the surface tension without influence of a vacuum above the drop as is the case with the prior art tube drop formers.

There has been described herein a drop former which can be mass produced with adequate assurances that the drops from each such drop former are of the exact precise same volume so that a controller, once calibrated to provide total volume administered as a function of drop rate can be used with each IV set.

What is claimed is:

1. In a metered drop dispenser device which includes a liquid reservoir, a drop forming means connected to the reservoir having an orifice at which drops of the liquid can be formed, a drop chamber coupled to the drop forming means through which drops fall and in which drops accummulate, a discharge device coupled to the bottom of the drop chamber for conveying the liquid to a utilization means, a metering means associated with the drop chamber for determining the drop rate, and drop rate control means to vary the drop rate, the improvement in the drop forming means comprising:

a pair of coplanar and spaced apart plate members having substantially parallel, planar facing end walls.

2. In a meter drop dispenser in accordance with claim 1 in which said plate members are of substantially uniform thickness.

3. In a metered drop dispenser in accordance with claim 2 in which said plate members are of substantially the same thickness.

4. In a metered drop dispenser in accordance with claim 3 in which said walls are separated a predetermined distance.

5. In a metered drop dispenser in accordance with claim 4 in which said end walls form a rectangular, elongated channel which is open on two sides.

6. In a metered drop dispenser in accordance with claim 5 in which the lower portion of said facing end walls are flared away from another to form flared end wall portions.

7. In a metered drop dispenser in accordance with claim 6 in which the thickness of said plate members, the separation of said end wall, the flare angle of said flared end wall portion and the length of said flared end wall portion are selected to form drops of a preselected volume.

* * * * *